United States Patent [19]

Boothe et al.

[11] Patent Number: 4,772,462

[45] Date of Patent: Sep. 20, 1988

[54] HAIR PRODUCTS CONTAINING DIMETHYL DIALLYL AMMONIUM CHLORIDE/ACRYLIC ACID-TYPE POLYMERS

[75] Inventors: Jerry E. Boothe, Coraopolis; Lewis D. Morse, Pittsburgh, both of Pa.; William L. Klein, Nutley, N.J.

[73] Assignee: Calgon Corporation, Pittsburgh, Pa.

[21] Appl. No.: 923,528

[22] Filed: Oct. 27, 1986

[51] Int. Cl.$^4$ .............................................. A61K 7/075
[52] U.S. Cl. ........................................ 424/70; 424/81; 252/DIG. 13
[58] Field of Search .................................. 424/70, 81; 252/DIG. 13

[56] References Cited

U.S. PATENT DOCUMENTS

| | | | |
|---|---|---|---|
| Re. 28,543 | 9/1975 | Boothe et al. | 428/514 |
| 3,761,417 | 9/1973 | Parran | 424/78 X |
| 3,769,398 | 10/1973 | Hewitt | 424/78 X |
| 3,912,808 | 10/1975 | Sokol | 424/70 X |
| 3,986,825 | 10/1976 | Sokol | 424/70 X |
| 3,996,146 | 12/1976 | Tarasov et al. | 424/DIG. 2 |
| 4,027,008 | 5/1977 | Sokol | 424/70 X |
| 4,040,984 | 8/1977 | Sharpe, Jr. et al. | 524/521 X |
| 4,329,335 | 5/1982 | Su et al. | 424/71 X |
| 4,348,380 | 9/1982 | Jacquet et al. | 424/65 X |
| 4,578,216 | 3/1986 | Fujii et al. | 252/DIG. 13 |
| 4,673,525 | 6/1987 | Small et al. | 252/117 X |

Primary Examiner—John E. Kittle
Assistant Examiner—Susan S. Rucker
Attorney, Agent, or Firm—W. C. Mitchell; M. C. Sudol, Jr.

[57] ABSTRACT

This invention relates to improved hair products which contain dialkyl diallyl ammonium chloride/acrylic acid-type polymers. These polymers provide exceptional conditioning properties to hair products such as shampoos, conditioners, rinses, bleaches, hair dyes and hair sprays.

8 Claims, No Drawings

HAIR PRODUCTS CONTAINING DIMETHYL DIALLYL AMMONIUM CHLORIDE/ACRYLIC ACID-TYPE POLYMERS

BACKGROUND OF THE INVENTION

The instant invention relates to improved hair products which contain at least one dimethyl diallyl ammonium chloride (DMDAAC)/acrylic acid-type polymer. These polymers provide exceptional hair conditioning benefits at low concentration, and are compatible with anionic systems.

Numerous references disclose cosmetic and personal care compositions such as shampoos, antiperspirant formulations, anti-dandruff rinse conditioners, etc., which contain anionic and/or cationic polymers, an active agent, surfactants, emollients and other additives and preservatives commonly employed in the industry. Pertinent references which relate to DMDAAC/acrylic acid polymers or which disclose cosmetic and personal care formulations containing anionic and cationic polymers include:

1. U.S. Pat. No. 3,761,417, which is directed to detergent compositions containing particle deposition enhancing agents. More particularly, this patent discloses detergent and personal use toilet detergent bars containing water-insoluble particles such as antimicrobial agents, organic surfactants and cationic polymers. Surfactants are an essential ingredient of these compositions, and DMDAAC is mentioned as a possible cationic polymer.

2. U.S. Pat. No. 3,769,398, which discloses non-ionic hair shampoo formulations containing an active ingredient such as a betaine, sulfo betaine, amine oxide or mixture thereof, a water soluble polymer such as a polyethyleneimine-ethylene oxide or propylene oxide polymer or a propoxylated polyethyleneimine.

3. U.S. Pat. No. 4,329,335, which describes an amphoteric, nonionic anti-dandruff shampoo containing an active agent (1-imidazalyl-1-)(chlorophenoxy-3,3-dimethylbutane-2-one) and amphoteric surfactants. DMDAAC is disclosed as a preferred quaternized ammonium compound in this patent.

4. Published European Patent Application No. 74,819, which discloses an anti-dandruff cream rinse conditioner containing zinc pyrithione, glucan or guar gum, hydroxyethyl cellulose and a homopolymer of DMDAAC or a copolymer of DMDAAC and acrylamide.

5. U.S. Pat. No. 3,996,146, which discloses a shampoo formulation comprising from 0.05 to about 2.5%, by weight, of a cationic resin including quaternary polymers derived from dimethyl diallyl ammonium salts.

6. U.S. Pat. No. 4,040,984, which discloses polymers useful for preparing electroconductive paper which comprise quaternary diallyl dialkyl ammonium monomers and acrylic acid.

7. U.S. Pat. No. 3,912,808, which discloses a composition and method for waving or straightening hair using an aqueous solution of a reducing agent and a water soluble secondary or tertiary amine polymer or a polymer of diallyl amine or a quaternary polymer of diallyl dialkyl ammonium salts. This patent also discloses the use of dialkyl ammonium polymers which contain acrylamide or diacetone acrylamide. The use of dimethyl diallyl ammonium chloride/acrylic acid polymers is not disclosed or suggested.

8. U.S. Pat. No. 4,027,008, which discloses hair treating compositions which contain a water soluble secondary or tertiary amine polymer or a polymer of diallyl amine or a quaternary polymer of diallyl dialkyl ammonium salts. This patent does not disclose or suggest the use of DMDAAC/acrylic acid polymers, and states that many widely used products for treating hair contain anionic surfactants which may inactivate cationic additives.

9. U.S. Pat. No. 3,986,825, which discloses the use of dialkyl diallyl ammonium polymers in cosmetic products, including copolymers of a dialkyl diallyl ammonium monomer and acrylamide or diacetone acrylamide. However, polymers containing these cationic moieties and acrylic acid are not disclosed or suggested.

In summary, though dialkyl diallyl ammonium polymers are widely used in cosmetic applications, the use of polymers containing a diallyl dialkyl ammonium monomer and acrylic acid is not known or suggested in the art. These polymers provide an increased level of cationic activity with unexpected compatibility in anionic systems.

DETAILED DESCRIPTION OF THE INVENTION

The instant invention is directed to a method for improving the conditioning properties of a hair product, comprising adding to said hair product an effective amount of a polymer comprising:

(a) about 60 to about 99%, based on total polymer weight, of a quaternary diallyl dialkyl ammonium monomer, wherein alkyl groups are independently selected from alkyl groups of 1 to 18 carbon atoms, preferably $C_{1-4}$ alkyl, and wherein said quaternary diallyl dialkyl ammonium monomer's counterion is selected from the group consisting of conjugate bases of acids having an ionization constant greater than $10^{-13}$, more preferably selected from the group consisting of fluoride, chloride, bromide, hydroxide, nitrate, acetate, hydrogen sulfate, and primary phosphates; and (b) about 1 to about 40%, based on total polymer weight, of an anionic monomer selected from the group consisting of acrylic acid and methacrylic acid; wherein the weight average molecular weight of said polymer ranges from about 50,000 to about 10,000,000, as determined by gel permeation chromatography.

The instant invention is also directed to improved hair products which contain the above described polymer.

As used herein, the term "hair product" includes, but is not limited to, conditioners, rinses, setting lotions, shampoos, bleaches, dyes, and hair sprays. The instant polymers provide slip, lubricity, and richness to foam, while improving wet combability in shampoo formulations. The instant polymers also impart to the treated hair a soft, silky feel, while providing antistatic properties and adding luster to dry hair. Also, buildup does not occur on the hair with repeated use.

Hair products generally comprise an active agent, stabilizers, conditioners, surfactants, emollients and other additives and preservatives commonly employed in the hair industry. For example, active agents may include dyes, bleaching agents such as hydrogen peroxide, hair waving and straightening agents, neutralizing agents and surfact active agents, including soaps and detergents. Typical active agents are fully described in U.S. Pat. No. 3,986,825, which is incorporated herein by reference.

The instant polymers, in addition to their conditioning benefits, may enhance dispersion and improve the efficacy of functional ingredients in hair products.

As used herein, the term "effective amount" refers to that amount of polymer required to improve the conditioning properties of the hair products being treated. Generally, the instant polymers are added at a dosage ranging from about 0.1% active polymer solids to about 5% active polymer solids, based on the total weight of the hair product to which the polymer is added. Preferably, the dosage ranges from about 0.2 to about 3%, based on the total weight of the hair composition being treated and most preferably from about 0.5% to about 2.5%, based on the total weight of the composition being treated.

The quaternary diallyl dialkyl ammonium monomer comprises from about 60 to about 99%, based on total polymer weight, while the anionic monomer comprises from about 1 to about 40%, based on total polymer weight. Preferably, the quaternary:anionic weight ratio is from about 95:5 to about 75:25, based on the total weight of the polymer. Thus, in the polymers of the present invention, the cationic portion of the polymer is predominant while the anionic portion of the polymer is minor. Additionally, other moieties may be present in the instant polymers.

An especially suitable polymer is that where the cationic portion is dimethyldiallyl ammonium chloride (DMDAAC) of diethyldiallyl ammonium chloride (DEDAAC) and where the anionic portion is acrylic acid. Preferably, the DMDAAC/DEDAAC:acrylic acid weight ratio ranges from about 99:1 to about 60:40, most preferably from about 95:5 to 75:25, based on total polymer weight.

The polymers of the instant invention may have any weight average molecular weight ranging from about 50,000 to about 10,000,000, as determined by gel permeation chromatography, with the preferred molecular weight ranging from about 200,000 to about 5,000,000. The most preferred viscosity for the instant polymers ranges from about 4,000 to about 10,000 cps, as determined using a Brookfield LVF No. 4 spindle at 60 rpm. These polymers may be prepared using any conventional free radical polymerization technique, such as the technique disclosed by Butler and Angelo, "Journal of American Chemical Society," Vol. 79, p. 3128 (1957) or the technique suggested in U.S. Pat. No. Re. 28,543. These references are incorporated by reference into this specification.

EXAMPLES

The following examples are not intended to limit the scope of this invention in any way.

Various water soluble polymers were tested to assess their benefits and usefulness in hair care products. Two major groups of polymers were evaluated, including homopolymers of dimethyldiallyl ammonium chloride (DMDAAC), for comparison, and copolymers of DMDAAC and acrylic acid (DMDAAC/AA).

The polymers were tested in solutions of deionized water and aqueous solutions containing an amphoteric surfactant. The solutions were then applied to hair and subjectively rated for slip, combability, flyaway, set (sword test), curl retention and substantivity.

These screening parameters are described below:

Screening parameters

All polymers were subjectively evaluated using the following parameters:

Slip: Slip is the subjective feel to the fingers of a hair swatch treated with a polymer solution.
Rating: 1 (very slippery) to 6 (feel with deionized water)
Combability: Combability is the subjective ease with which a treated swatch of hair is detangled.
Rating: 1 (easy) to 6 (difficult)
Flyaway: Flyaway is the angle formed by the outermost hairs of a swatch deflected by the generation of static charge after combing.
Rating: 1 (22.5°) to 8 (180°)
Sword Test: The sword test measures hair set. The angle from the horizontal formed by a dried hair bundle when held at one end in a horizontal plane is determined.
Rating: 1 (90°) to 8 (11.5°)
Curl Retention: Curl retention is the amount of curl retained over time after unwinding hair dried on rollers.

$$\%\text{Retention} = \frac{L - Lt}{L - Lo} \times 100$$

Where:
L = Length of hair fully extended
Lo = Length of hair before exposure (initial value)
Lt = Length of hair after exposure for time (t)
Substantivity: Substantivity is a measure of polymer retention on hair. A treated natural white hair swatch was dyed with a macro polyanionic red dye (Rubine). The intensity of the red color on the hair was a function of the substantivity of the cationic polymer on the hair.
Rating: 1 (dark red) to 10 (deionized water control)

All polymers were tested at a 1% w/w active polymer concentration. One gram of polymer solution was worked into a 2 gram swatch of natural white virgin hair by hand and rinsed.

The amphoteric surfactant solution used was 6% w/w active cocamidopropyl betaine.

The following polyDMDAAC samples were screened:

| Sample Designation | Weight % Polymer | Intrinsic* Viscosity (dl/g) | RV Brookfield Viscosity (cps) | Spindle Number | rpm |
|---|---|---|---|---|---|
| A | 35.9 | 1.97 | 236,000 | 7 | 10 |
| B | 37.7 | 0.92 | 15,800 | 7 | 100 |
| C | 35.4 | 0.55 | 2,264 | 6 | 100 |
| D | 29.6 | 0.10 | 57 | 1 | 100 |

The following DMDAAC/AA polymers were screened:

| Sample Designation | Weight % Polymer | DMDAAC/AA Ratio (w/w) | Intrinsic* Viscosity (dl/g) | RV Brookfield Viscosity @ 25° C. (cps) | Spindle Number | rpm |
|---|---|---|---|---|---|---|
| E | 22.9 | 70/30 | 0.16 | 52 | 1 | 100 |
| F | 22.9 | 50/50 | 0.37 | 180 | 2 | 100 |

-continued

| Sample Designation | Weight % Polymer | DMDAAC/AA Ratio (w/w) | Intrinsic* Viscosity (dl/g) | RV Brookfield Viscosity @ 25° C. (cps) | Spindle Number | rpm |
|---|---|---|---|---|---|---|
| G | 32.1 | 70/30 | 0.43 | 586 | 4 | 100 |
| H | 27.5 | 60/40 | 0.44 | 267 | 3 | 100 |
| I | 32.1 | 50/50 | 0.62 | 9,460 | 4 | 10 |
| J | 32.1 | 80/20 | 0.36 | 457 | 2 | 50 |

*Intrinsic viscosities were measured using a Ubbelohde viscometer.

EXAMPLES 1-10

Results of the screening tests for these samples appear in Tables I and II for the deionized water and amphoteric systems, respectively.

TABLE I

Deionized Water

| Example Number | Sample Designation | Slip 1 6* | Combability 1 6* | Sword Test 1 8* | Flyaway 1 8* |
|---|---|---|---|---|---|
| 1 | Control (No Polymer) | 6 | 5 | 5 | 2 |
| 2 | Poly(DMDAAC) A | 1 | 5 | 5 | 7 |
| 3 | Poly(DMDAAC) B | 2 | 5 | 5.5 | 6 |
| 4 | Poly(DMDAAC) C | 3 | 4 | 6 | 6 |
| 5 | Poly(DMDAAC) D | 4 | 5 | 5 | 6 |

*Rating of 1 = excellent

TABLE II

| | | Amphoteric Surfactant | | | | |
|---|---|---|---|---|---|---|
| Example Number | Sample Designation | Slip 1-6* | Combability 1-6* | Sword Test 1-8* | Flyaway 1-8* | Substantivity 1-10* |
| 6 | Control (No Polymer) | 6 | 5 | 5 | 1 | 10 |
| 7 | Poly(DMDAAC) A | 1 | 2 | 6 | 7 | 2 |
| 8 | Poly(DMDAAC) B | 1 | 3 | 6 | 5 | 3 |
| 9 | Poly(DMDAAC) C | 3 | 4 | 6 | 6 | 3 |
| 10 | Poly(DMDAAC) D | 3 | 5 | 5 | 5 | 3 |

*Rating of 1 = excellent

EXAMPLES 11-20 (DMDAAC/AA)

Results of the screening tests for these samples appear in Tables III (amphoteric surfactant) and IV (amphoteric surfactant and deionized systems).

An 80/20 DMDAAC/AA polymer, having a weight average molecular weight of approximately 1,300,000, as determined by gel permeation chromatography, (Merquat 280) and five additional samples having modified ratios were prepared for evaluation.

TABLE III

| | | Amphoteric Surfactant | | | |
|---|---|---|---|---|---|
| Example Number | Sample Designation | Slip 1-6* | Combability 1-6* | Curl Retention % | Flyaway 1-8* | Substantivity 1-10* |
| 11 | Control (No Polymer) | 5 | 7.5 | 58.8 | 3.75 | 10 |
| 12 | DMDAAC/AA 70/30 E | 5 | 6 | 67.3 | 1.38 | 6 |
| 13 | DMDAAC/AA 50/50 F | 4.5 | 7 | 67.1 | 4 | 9 |
| 14 | DMDAAC/AA 70/30 G | 4.75 | 6 | 73.9 | 2.88 | 8 |
| 15 | DMDAAC/AA 60/40 H | 4.5 | 6.5 | 74.6 | 2.25 | 6.5 |
| 16 | DMDAAC/AA 50/50 I | 4 | 6 | 77.2 | 3 | 8 |

*Rating of 1 = excellent

TABLE IV

| Sample Number | Sample Designation | Slip 1-6* | Combability 1-6* | Curl Retention % |
|---|---|---|---|---|
| | | Amphoteric Surfactant | | |
| 17 | Control (No Polymer) | 5 | 7 | 57.4 |
| 18 | DMDAAC/AA 80/20 J (Merquat 280) | 3 | 5 | 60.8 |
| | | Deionized Water | | |
| 19 | Control | 6 | 9 | 47.9 |
| 20 | DMDAAC/AA 80/20 | 5 | 4 | 52.0 |

TABLE IV-continued

| Sample Number | Sample Designation | Slip 1–6* | Combability 1–6* | Curl Retention % |
|---|---|---|---|---|
| | J (Merquat 280) | | | |

*Rating of 1 = excellent

For samples E, F, G, H and I, slip and combability improved slightly with increasing molecular weight.

Percent Curl Retention improved dramatically with increasing molecular weight. Flyaway improved with the 70/30 and 60/40 samples. Rubine substantivity decreased with increasing % AA. These results indicate the DMDAAC/AA polymer of choice should have a high molecular weight and low % AA.

EXAMPLES 21 AND 22

These samples demonstrate the use of the instant polymers in hair product formulations.

EXAMPLE 21

CONDITIONING SHAMPOO

A clear viscous shampoo formulation was prepared using the following ingredients and in accordance with the following instructions to demonstrate the excellent compatibility of the instant polymers with anionic surfactants. Compatibility of Merquat 280, which has a net cationic charge density, with an anionic system is surprising and unexpected.

| Ingredients | % w/w |
|---|---|
| A - Deionized Water | 59.40 |
| Sodium Lauryl Sulfate | 30.00 |
| PEG 150 Distearate | 0.40 |
| Lauramide DEA[1] | 2.00 |
| Cocamide MEA[2] | 2.00 |
| B - Sodium Lauryl Sarcosinate | 4.00 |
| MERQUAT 280[3] | 2.00 |
| C - Tetrasodium EDTA[4] | 0.20 |
| Citric Acid | As Desired to pH 6.5 |

Preparation Instructions

Heat water to 75° C. Add ingredients listed in Part A in the order stated. Proceed after each addition is clear and uniform. Maintain 70°–75° C. Premix the MERQUAT 280 in the Sodium Lauroyl Sarcosinate and add as Part B at 50° C. Add Part C at 40° C. Adjust pH to 6.5 with citric acid. Optionally, fragrances, preservatives and dyes can be added. Viscosity: 2000 cps.

1. Lauramide DEA is lauryl diethanolamine.
2. Cocamide MEA is coco monoethanolamine.
3. MERQUAT 280 is an 80/20 w/w polymer of DMDAAC and acrylic acid having a viscosity (Brookfield LVF, #4 spindle @30 rpm) of 4,000–10,000 cps, commercially available from Calgon Corporation and a Mw of approximately 1,300,000.
4. Tetrasodium EDTA is the sodium salt of ethylenediamine tetracetic acid.

EXAMPLE 22

Cationic Creme Rinse

A cream rinse formulation was repared using the following ingredients and in accordance with the following instructions.

This creme rinse containing MERQUAT 280 left hair soft, lustrous and oil-free.

| Ingredients | % W/W |
|---|---|
| A - Deionized Water | 95.25 |
| Natrosol 250 HR[1] | 0.75 |
| B - Polawax[2] | 2.00 |
| Cetearyl Alcohol[3] | 2.00 |
| Laureth 23[4] | 1.00 |
| C - MERQUAT 280[5] | 2.00 |
| D - Lactic Acid | to pH 4.0 |

Preparation Instructions

Using high speed agitation slowly sprinkle the Natrasol 250 HR into the water. Continue mixing until completely hydrated. Continue mixing and heat Part A to 75° C. In a separate vessel heat the ingredients of Part B to 75° C. Slowly add Part B to Part A. Continue mixing and begin cooling when uniform. Continue mixing and cooling and add MERQUAT 280 at 35° C. Adjust pH to 4.0 with lactic acid. Optionally, fragrances, preservatives and dyes may be used.

1. Natrosol 250 HR is hydroxyethyl cellulose, commercially available from Hercules.
2. Polawax is a commercially available emulsifying wax.
3. Cetearyl Alcohol is a 50/50 mixture cetyl alcohol and stearyl alcohol available from Henkel.
4. Laureth 23 is a polyethylene glycol dodecyl ether, available from Marinol Chemical.
5. MERQUAT 280 is an 80/20 w/w copolymer of DMDAAC and acrylic acid (see description, Example 21).

What is claimed is:

1. A method for improving conditioning properties of a hair product comprising adding to said hair product an effective amount of a polymer comprising:
   (a) about 60 to about 99%, by weight of said polymer, of a quaternary diallyl dialkyl ammonium monomer, wherein alkyl groups are independently selected from alkyl groups of 1 to 18 carbon atoms and wherein said quarternary diallyl dialkyl ammonium monomer's counterion is selected from the group consisting bases of acids having an ionization constant greater than $10^{-13}$.
   (b) about 1 to about 40A%, by weight of said polymer, of an anionic monomer selected of the group consisting of acrylic acid and methacrylic acid; wherein the weight average molecular weight of said polymer ranges from about 50,000 to about 10,000,000, as determined by gel permeation chromatography.

2. The method of claim 1, wherein said alkyl group of (a) is $C_{1-4}$.

3. The method of claim 1, wherein (a) is selected from the group consisting of dimethyldiallyl ammonium chloride and diethyldiallyl ammonium chloride and (b) is acrylic acid.

4. The method of claim 1 wherein said effective amount ranges from about 0.1 to about 5%, by weight, of said hair additive.

5. The method of claim 1 wherein said hair additive comprises an active agent and a surfactant.

6. The method of claim 5, wherein said surfactant is anionic.

7. The method of claim 1, wherein said counterion is selected from the group consisting of fluoride, chloride, bromide, hydroxide, nitrate, acetate, hydrogen sulfate and primary phosphates.

8. An improved hair product which comprises:

a. an active agent;
b. an anionic surfactant;
c. a copolymer comprising;
  1. about 60 to about 99%, by weight of said polymer, of a monomer selected from the group consisting of dimethyldiallyl ammonium chloride and diethyldiallyl ammonium chloride; and
  2. about 1 to about 40%, by weight of said polymer, a monomer selected from the group consisting of acrylic acid, and methacrylic acid, wherein said polymer has a weight average molecular weight ranging from about 50,000 to about 10,000,00, as determined by gel permeation chromatography.

* * * * *